US00PP13026P2

(12) United States Plant Patent
Michalik

(10) Patent No.: US PP13,026 P2
(45) Date of Patent: Oct. 1, 2002

(54) VARIETY OF GERANIUM PLANT NAMED 'FIWOCHER'

(75) Inventor: Andrea Michalik, Dresden (DE)

(73) Assignee: Elsner pac Jungplanzen (DE)

( * ) Notice: Subject to any disclaimer, the term of this patent is extended or adjusted under 35 U.S.C. 154(b) by 0 days.

(21) Appl. No.: 09/733,021

(22) Filed: Dec. 8, 2000

(51) Int. Cl.[7] ..... A01H 5/00
(52) U.S. Cl. ..... Plt./325
(58) Field of Search ..... Plt./330, 325, 324

*Primary Examiner*—Kent L. Bell
(74) *Attorney, Agent, or Firm*—Webb Ziensenheim Logsdon Orkin & Hanson, P.C.

(57) ABSTRACT

A new and distinct zonal geranium plant with red flowers above medium green foliage. The plant is suitable for planting in pots or as a bedding plant.

1 Drawing Sheet

BOTANICAL/COMMERCIAL CLASSIFICATION

*Pelargonium×hortorum*; Zonal Geranium.

VARIETY DENOMINATION

'FIWOCHER'.

BACKGROUND OF THE INVENTION

The present invention comprises a new and distinct cultivar of *Pelargonium×hortorum* known by the varietal name 'Fiwocher'. The new variety was discovered in 1998 in a selective breeding program in Dresden, Germany. The new variety is the result of a cross between two unnamed and unpatented selections from breeding group 7-K -34, which comprises about 60 stellar-type breeding varieties with red and white flowers. The new variety has a more intense flower color than its parental cultivars. The new variety also has bicolored flowers but its parental cultivars do not. The new variety was first asexually reproduced by cuttings in Dresden, Germany in 1999. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these charactertistics were collected by asexual reproductions carried out in Dresden, Germany. The color readings were taken outdoors in diffuse light. Color references are primarily to The R.H.S. Colour Chart of The Royal Horticultural Society of London. The instant cultivar was 9 months old and in a container having a diameter of 15 cm when described.

PLANT

Form: Erect.
Height from media surface to top of foliage: 50 cm.
Height from media surface to top of umbel: 65 cm.

Width: 32–35 cm.
Growth: High degree of branching.
Strength: Does not require artificial support.
Response time: 3.5 weeks.
Leaves:
- *Length.*—5 cm.
- *Width.*—6.5 cm.
- *Shape.*—Maple leaf-shaped.
- *Margin.*—Entire; deeply indented.
- *Texture.*—Smooth, some pubescence.
- *Color.*—Upper surface: Green Group 139B with zone of Yellow-Green Group 147B. Lower surface: Green Group 138B.
- *Ribs and veins.*—Color: Green Group 137B.

Petioles:
- *Color.*—Green Group 138A.
- *Length.*—3–5 cm.
- *Diameter.*—0.3 cm.

Stem/branches:
- *Color.*—Green Group 138A.
- *Length.*—24 cm.
- *Internode length.*—3–5 cm.

THE BUD

Shape when just showing color:
- *Overall.*—Semi-spherical.
- *Individual bud.*—Narrow; elliptical.

Color: Green Group 143B.
Size when just showing color:
- *Umbel.*—8–10 cm across.
- *Individual bud.*—1–1.7 cm long; 0.5 cm wide.

INFLORESCENCE

Blooming habit: Star-like; single.
Size of fully open bloom: 2.5–3.5 cm across. Depth of 8–9 cm.
Average number of inflorescences per plant: 30–50 per season.
Borne: Umbel; flowers on pedicel; pedicel on peduncle.
Flowers:
- *Form.*—Zygomorph.
- *Number of petals.*—5.
- *Size.*—Upper petals: 0.5–0.7 cm wide; 1.7 cm long. Lower petals: 0.7–1.0 cm wide; 1.7 cm long.

*Petals.*—Color: Upper surface: Red Group 52A. Lower surface: Red Group 52A. Eye: White.
*Texture and appearance.*—Velvety.
*Apex.*—Pointed.
*Base.*—Pointed.
*Margin.*—Serrated.
Petaloids: Absent.
Pedicel:
*Length.*—3–3.5 cm.
*Color.*—Green Group 137B.
Peduncle:
*Length.*—15 cm.
*Color.*—Green Group 138A.
Sepals:
*Quantity.*—5.
*Length.*—0.5 cm.
*Width.*—0.2 cm.
*Apex.*—Pointed.
*Base.*—Wide (not pointed).
*Margin.*—Smooth.
*Color.*—Upper surface: Green Group 139C. Lower surface: Green Group 139C.
Disease/pest resistance: No susceptibility to diseases or pests has been noted to date.
Lasting quality: Long-lasting; 3–4 weeks per umbel.

REPRODUCTIVE ORGANS

Stamens:
*Anthers.*—3 mm long.
*Filaments.*—Length: 0.5 cm maximum. Color: White with greenish shine.
*Pollen.*—Dark yellow.
Pistils:
*Number.*—One, five parted.
*Length.*—0.3–0.4 cm.
*Stigma.*—White in color.
*Style.*—0.8 cm long.
Ovaries:
*Color.*—Greenish.
*Length.*—0.4 cm.
Fruit: Present with 5 seeds; fruit production very weak.

GENERAL CHARACTERISTICS

1. Maple leaf-shaped foliage.
2. Erect, compact growth.
3. Good branching.
4. Flowers single, star-like, two-colored.
5. Long-lasting with high resistance against rain.
6. Low care requirements.

I claim:

1. A new and distinct variety of geranium plant substantially as shown and described.

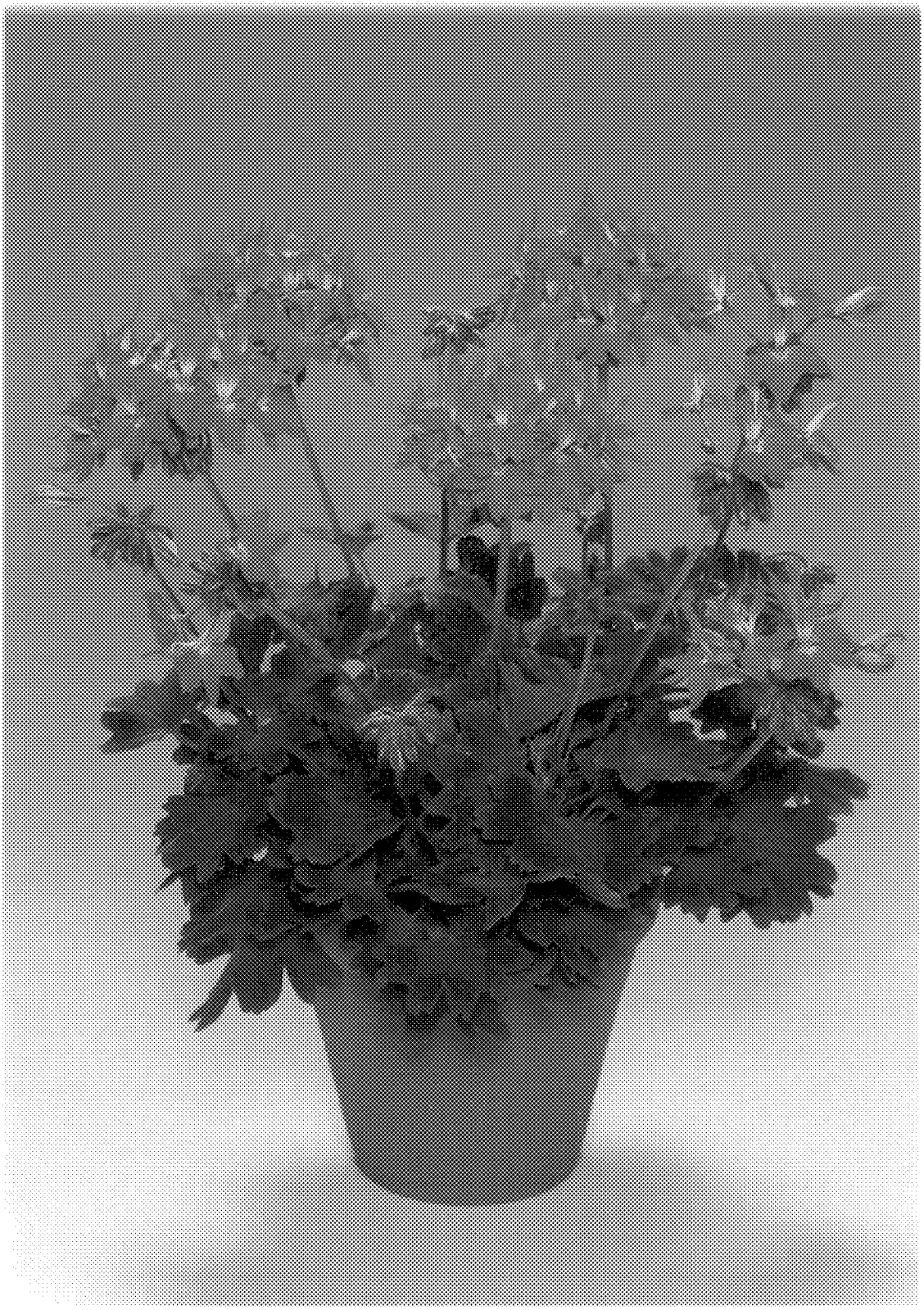

* * * * *